(12) United States Patent
Hoffmann et al.

(10) Patent No.: US 11,129,635 B2
(45) Date of Patent: Sep. 28, 2021

(54) MEDICAL INSTRUMENT

(71) Applicant: Karl Storz SE & Co. KG, Tuttlingen (DE)

(72) Inventors: Martin Hoffmann, Tuttlingen (DE); Jonas Forster, Tuttlingen (DE); Simon Albrecht, Berlin (DE); Gordon Böse, Berlin (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 44 days.

(21) Appl. No.: 16/781,171

(22) Filed: Feb. 4, 2020

(65) Prior Publication Data

US 2020/0253626 A1   Aug. 13, 2020

(30) Foreign Application Priority Data

Feb. 12, 2019   (DE) ................... 10 2019 103 493.0

(51) Int. Cl.
*A61B 17/29* (2006.01)
*A61B 17/00* (2006.01)

(52) U.S. Cl.
CPC .... *A61B 17/29* (2013.01); *A61B 2017/00867* (2013.01); *A61B 2017/2902* (2013.01);
(Continued)

(58) Field of Classification Search
CPC ............ A61B 17/29; A61B 2017/0069; A61B 2017/00867; A61B 2017/2902;
(Continued)

(56) References Cited

U.S. PATENT DOCUMENTS 4,753,626 A * 6/1988 Hazebrook ............. B25B 13/06
464/140
8,142,473 B2   3/2012 Cunningham
(Continued)

FOREIGN PATENT DOCUMENTS

DE           103 14 828 B3   7/2004
DE   10 2015 015 655 A1   6/2017
(Continued)

OTHER PUBLICATIONS

Search Report, DE 10 2019 103 493.0, dated Jan. 14, 2020 (9 pp.).
Search Report for EP 20155030.8, dated Jul. 1, 2020 (8 pp.).

*Primary Examiner* — Brooke Nicole Labranche
(74) *Attorney, Agent, or Firm* — Eversheds Sutherland (US) LLP (57) ABSTRACT

The application relates to a medical instrument with a hollow shaft, with a handle at the proximal end and a tool with two jaw parts at the distal end, of which at least one jaw part is pivotable, wherein a distal end region of the shaft is configured as a deflectable, rotatable tool tip, and wherein the jaw parts are adjustable between closed and open positions, wherein rotation of the tool tip and actuation of the jaw parts take place via actuation elements coupled at the proximal end to the handle. The distal end of the shaft and the proximal end of the tool tip are arc-shaped, and roll on each other for the deflection of the tool tip, and are conveyed from the shaft into the deflectable tool tip via at least two identical joints, which are connected in series and which can transmit rotation and translatory movements.

8 Claims, 6 Drawing Sheets

(52) U.S. Cl.
CPC ............... *A61B 2017/2923* (2013.01); *A61B 2017/2927* (2013.01); *A61B 2017/2947* (2013.01)

(58) Field of Classification Search
CPC ...... A61B 2017/292; A61B 2017/2923; A61B 2017/2927; A61B 2017/2929; A61B 2017/2947; A61B 17/28
See application file for complete search history.

(56) References Cited

U.S. PATENT DOCUMENTS

| | | |
|---|---|---|
| 9,216,013 B2 | 12/2015 | Scirica et al. |
| 2004/0225323 A1 | 11/2004 | Nagase et al. |
| 2009/0320637 A1 | 12/2009 | Doyle et al. |
| 2010/0320252 A1* | 12/2010 | Viola ............... A61B 17/07207 227/176.1 |
| 2016/0242800 A1 | 8/2016 | Melsheimer et al. |
| 2017/0120457 A1 | 5/2017 | Saraliev et al. |
| 2019/0336157 A1* | 11/2019 | Ahrens ................ A61B 17/295 |

FOREIGN PATENT DOCUMENTS

| | | |
|---|---|---|
| EP | 0 596 213 A1 | 11/1994 |
| EP | 2 413 819 A1 | 2/2012 |
| WO | 2019136041 A1 | 7/2019 |

\* cited by examiner

MEDICAL INSTRUMENT

TECHNICAL FIELD

The invention relates to a medical instrument with a hollow shaft, at the proximal end of which a handle is arranged, and at the distal end of which a tool with two jaw parts is arranged, of which at least one jaw part is pivotable relative to the other jaw part, wherein a distal end region of the shaft that carries the tool is configured as a tool tip that can be deflected with respect to the longitudinal axis of the shaft, and the tool tip is rotatable about the longitudinal axis of the shaft respectively about the longitudinal axis of the tool tip, and wherein the at least one pivotable jaw part of the tool is adjustable between a closed position and an open position, wherein the rotation of the tool tip and the actuation of the jaw parts take place via actuation elements which are mounted in the shaft and which are coupled at the proximal end to the handle.

BACKGROUND OF THE INVENTION

Manually guided surgical instruments for minimally invasive operations, which afford the operating surgeon several degrees of freedom for the actuation of the instrument head respectively the tool tip, are known from practice in various embodiments. All of these instruments seek to provide the greatest possible stiffness while having the smallest possible external dimensions. Since instruments for use in endoscopic surgery need to be very small but at the same time need to grip very forcibly or permit cutting, the load on the joints and on the associated actuation mechanisms is very great.

Most of the known hinged instruments that are guided manually have a kinematics system closely fitted to the specific task that is to be performed in each case. To be able to provide the instrument head respectively the tool tip with the required degrees of freedom for the tasks involved, these known instruments in most cases have a larger shaft diameter than instruments that are not hinged.

To be able to transmit sufficient forces in deflectable types of instruments, it is known, from the instruments known in practice, to use control cables or bevel gear transmissions. In the case of control cables, which are well suited for transmitting sufficiently high forces, it often happens that organic material from the operating site catches between the individual strands of the control cables and is pulled into the shaft. These items of contamination of the control cables can be removed again only with very great difficulty during the cleaning of the instruments. In addition, with the very small bending radii that are needed in the instrument heads, the control cables are not durable, as a result of which the period of use of these instruments is only a limited one.

The instruments with bevel gear transmissions generally provide good articulation, are easy to clean and durable, but the power density is not so high as in instruments with control cables, for which reason either the maximum transmissible force is low or else the instrument needs to have a larger external diameter.

SUMMARY OF THE INVENTION

Proceeding from this, the object of the invention is to create a medical instrument of the type mentioned at the outset, in which instrument the joints ensure a high transmission force, along with the greatest possible number of degrees of freedom and a small installation space, and are also easy to clean.

This object is achieved according to the invention by the fact that, in order to configure a joint for the deflection of the tool tip, the distal end of the shaft and the proximal end of the tool tip are configured arc-shaped, and the two arcs roll on each other for the deflection of the tool tip, and in that the movements of the two actuation elements, for rotating the tool tip and for actuating the jaw parts, are conveyed from the shaft into the deflectable tool tip via at least two identical joints, which are connected in series one behind the other and which can transmit rotation movements and also translatory movements.

Since the joint for the deflection of the tool tip is configured in the shape of arcs that roll on each other, it is possible, within the drivetrain for the tool tip, that no lengthwise offset occurs that has to be compensated, which lengthwise offset would otherwise cause a constrained actuation of the jaw parts of the tool during the deflection of the tool tip.

Since the drivetrain for conveying the movements of the two actuation elements, for rotating the tool tip and for actuating the jaw parts, from the shaft into the deflectable tool tip is configured in the form of at least two identical joints connected in series one behind the other, it is possible for each of the at least two joints to be of small dimensions and, by virtue of the connection in series, it is possible to ensure the high degree of articulation that is desired.

According to a practical embodiment of the invention, it is proposed that the two arcs are configured as gearwheel profiles that roll on each other. The configuration as gearwheel profiles that roll on each other is a particularly simple design solution which, on account of the form-fit and frictional engagement occurring between the teeth on both sides, makes it possible to maintain the tool tip in a wide variety of deflected positions.

In order to configure the tooth profiles, it is proposed, according to a preferred embodiment of the invention, that the distal end of the shaft and the proximal end of the tool tip are each configured bifurcated, having two webs arranged at a distance from and parallel to each other, wherein the gearwheel profiles are configured at the free ends of the webs of the shaft and of the tool tip. By virtue of the fact that the tooth profiles forming the joint for the deflection of the tool tip are shifted to the lateral webs of the bifurcated ends, sufficient space remains in the middle of the shaft and of the tool tip for passage of the drivetrain for the tool tip.

The invention further proposes that the distal end of the shaft and the proximal end of the tool tip are connected to each other by two brackets, which are fixed to the webs at the midpoints of the gearwheel profiles. The two brackets hold the two sets of gearwheel profiles at a constant spacing from each other and thereby ensure a uniform rolling of the gearwheel profiles on each other, substantially free of play, during the deflection of the tool tip.

According to the invention, the deflection of the tool tip with respect to the longitudinal axis of the shaft is actuated via two pull/push elements which are guided in the shaft and are fixed at the distal end to the tool tip, and which are advantageously configured as rectangular nitinol bands. The smooth surfaces of the bands can be easily cleaned and, on account of their rectangular shape, utilize the available installation space better than circular elements, for example control cables.

According to a first practical embodiment for configuration of the drivetrain which conveys the movements of the two actuation elements, for rotating the tool tip and for actuating the jaw parts, from the shaft to the deflectable tool tip, the invention proposes that the at least two joints connected in series one behind the other are configured as CVD cardan joints.

Similarly to a known cardan joint, the constant velocity drive (CVD) joint is based on a rotary cross which however, in contrast to the known cardan joint, is not mounted in bifurcated recesses of the bearing axle but instead runs inside a holed ball. Since the CVD joint is located inside a holed ball, the joint can take up very high forces by virtue of the ball shape. The CVD joint can transmit pushing and pulling forces while it is tilted about two axes. Each CVD joint in itself permits the transmission of pushing and pulling movements and rotation movements when the joint is deflected by an angle of up to 45°. Therefore, since at least two identical CVD joints are connected in series according to the invention, a deflection of at least 90° is attainable.

With an alternative second practical embodiment for configuration of the drivetrain, it is proposed according to the invention that the at least two joints connected in series one behind the other are configured as homokinetic joints.

Homokinetic joints are characterized by the fact that they permit uniform transmission of angular velocity and torque from one shaft to a shaft arranged at an angle to the latter. The homokinetic joints are composed of a ball socket and a ball head, which seats in the ball socket. Both structural parts have up to six grooves which are formed axially along the ball surfaces of ball socket and ball head, wherein a groove of the ball head and a groove of the ball socket in each case form a groove pairing, in which a ball is guided in a constrained manner.

Each homokinetic joint in itself permits the transmission of a torque in the event of a deflection between input and output shaft of up to 45°. Therefore, since at least two identical homokinetic joints are connected in series according to the invention, a deflection of at least 90° is attainable. With the customary homokinetic joints, axial forces are transmissible only to a slight extent on account of the grooves of the ball tracks extending in the axial direction.

In order to markedly improve the transmission of axial forces by means of a homokinetic joint, it is proposed according to the invention that a ball head and a ball socket of each homokinetic joint are connected to each other via a wire which is arranged in the interior of the homokinetic joint and is mounted in the cardan shafts. By virtue of the wire internally bridging the joint, the ball socket and the ball head are fixed to each other in such a way that, without limiting the mobility of the homokinetic joint, high axial forces can now also be transmitted by means of a homokinetic joint thus modified.

According to a practical embodiment for configuration of this homokinetic joint that transmits axial forces, the invention proposes that an axial bore in the ball socket and in the ball head guides the wire, wherein the wire is connected to both components, i.e. the ball socket and the ball head.

Finally, the invention proposes that the wire is configured as a nitinol wire. The material nitinol is a shape-memory alloy which, after deformation can be automatically converted back again to its previous shape by heating.

Further features and advantages of the invention will become clear from the attached drawings in which two illustrative embodiments of a medical instrument according to the invention are shown simply by way of example, without limiting the invention to these illustrative embodiments. In the drawings:

DETAILED DESCRIPTION

Figure 1:
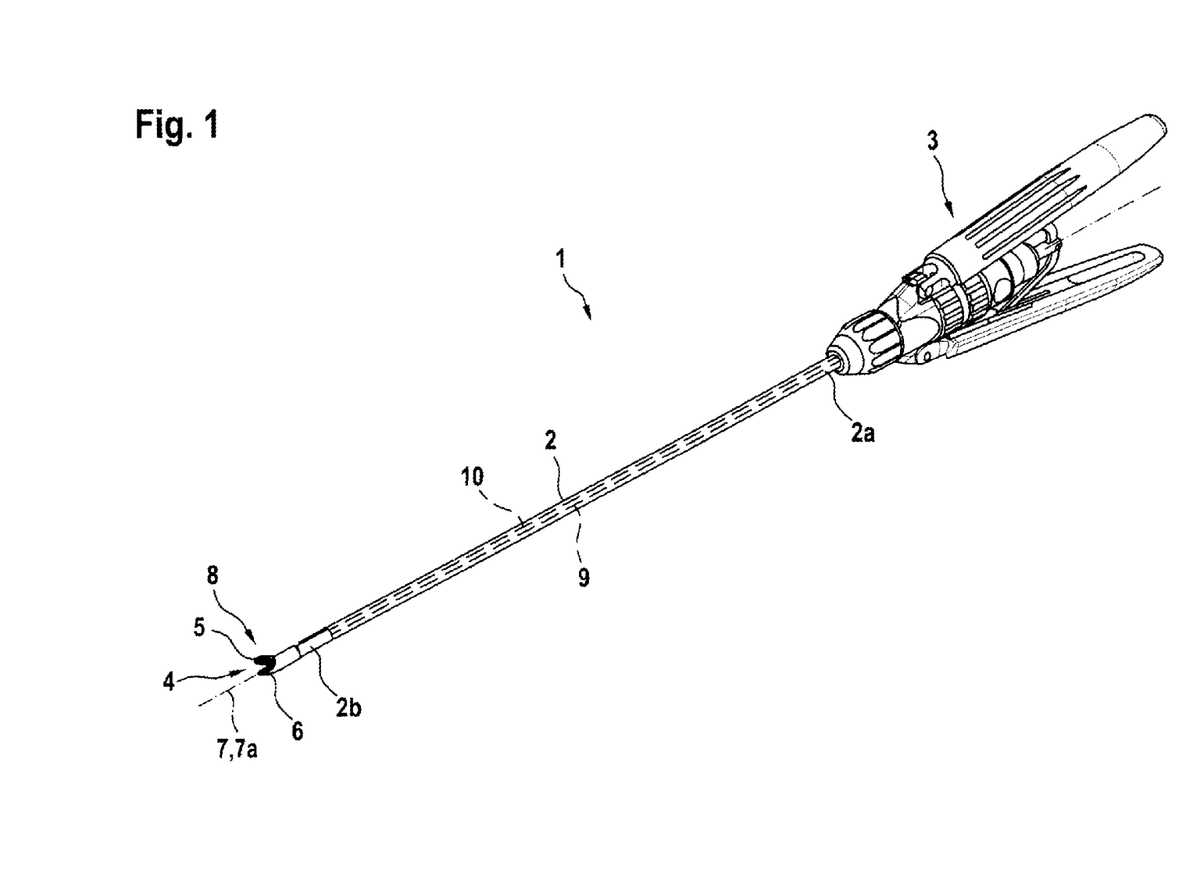
FIG. 1 shows a perspective side view of a medical instrument according to the invention.

FIG. 1 shows a medical instrument 1 with a hollow shaft 2, at the proximal end 2a of which a handle 3 is arranged, and at the distal end 2b of which a tool 4 is arranged consisting of two jaw parts 5, 6 which, in the embodiment described in more detail below, are configured as jaw parts 5 and 6 that are pivotable relative to each other.

In order to afford the tool 4 the greatest possible number of degrees of freedom relative to the shaft 2, a distal end region of the shaft 2 that carries the tool 4 is configured as a tool tip 8 that is deflectable with respect to the longitudinal axis 7 of the shaft 2. Moreover, the tool 4 is rotatable about the longitudinal axis 7 of the shaft 2 respectively, with the tool tip 8 deflected, about the longitudinal axis 7a of the tool tip 8.

In order to pivot the jaw parts 5 and 6 of the tool 4 relative to each other between a closed position and an open position, an axially movable first actuation element 9 is mounted in the shaft 2, the proximal end of said actuation element 9 being operatively connected to the handle 3.

The rotation of the tool tip 8 about the longitudinal axis 7 of the shaft 2 respectively the longitudinal axis 7a of the tool tip 8 takes place via a second actuation element 10 mounted rotatably in the hollow shaft 2.

A main problem in the production of medical instruments 1 of this kind is, on the one hand, to maintain all degrees of freedom while ensuring that the diameter of the shaft 2 is as small as possible, and, on the other hand, to configure a drivetrain 11 for conveying the movements of the two actuation elements 9 and 10, for rotating the tool tip 8 and for actuation of the jaw parts 5 and 6, from the shaft 2 into the deflectable tool tip 8, such that said drivetrain 11 is easy to clean and at the same permits a good transmission of force to the tool 4.

FIG. 2 to FIG. 5 show the configuration of a joint 12 via which the tool tip 8 is deflectable relative to the shaft 2 at an angle of up to 90°.

In most medical instruments known from the prior art having a deflectable tool tip, the deflection of the tool tip is effected about a rigid axle, wherein the pivot point about which the tool tip can be deflected relative to the shaft lies on the longitudinal axis of the shaft. However, this configuration of the deflection joint necessarily entails, during the deflection of the tool tip, a lengthwise offset in the drivetrain for actuation of the tool tip. Without compensation, this lengthwise offset of the drivetrain has the effect that, during the deflection of the tool tip, the jaw parts of the tool are also necessarily actuated at least slightly.

Figure 2:
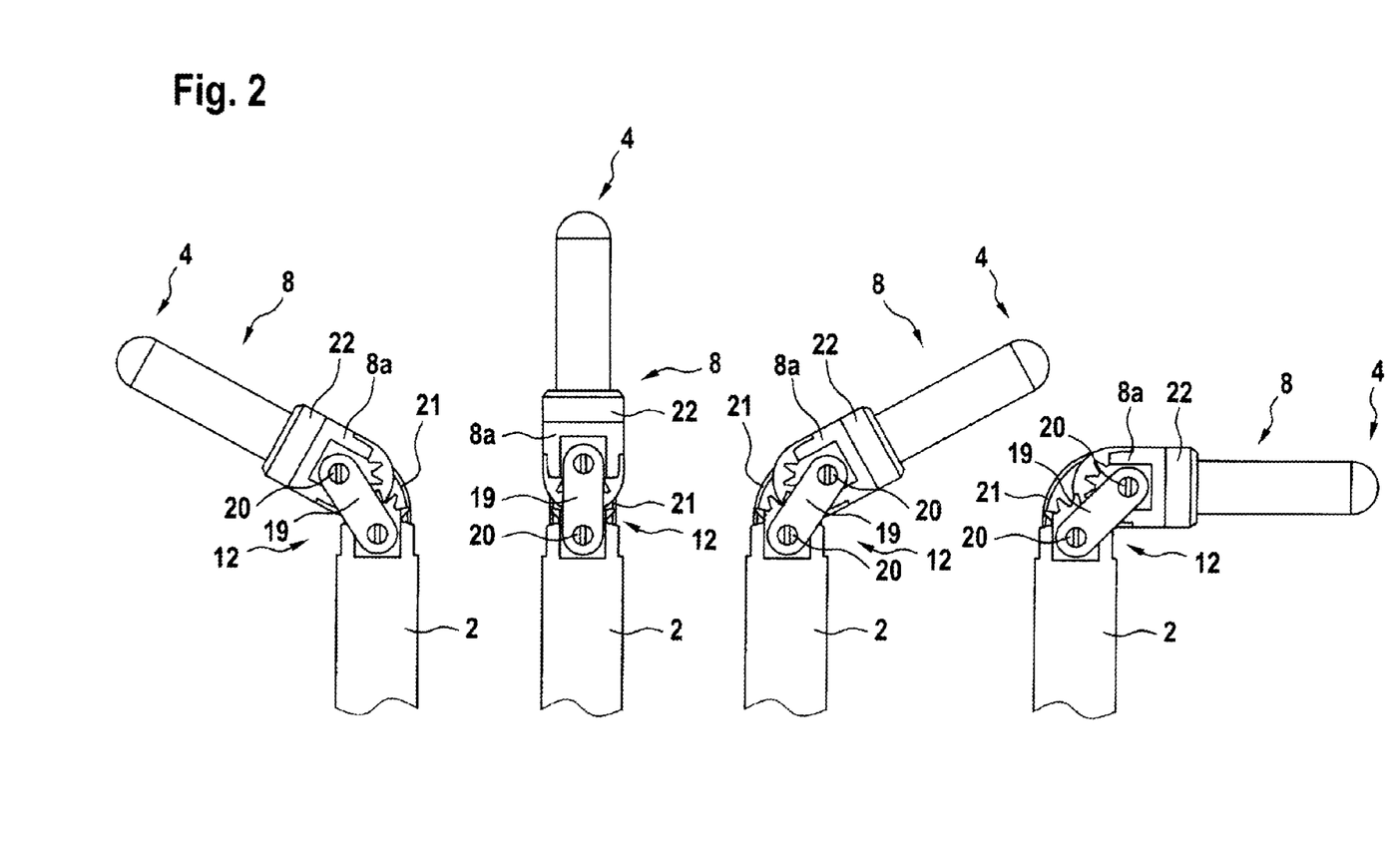
FIG. 2 shows a side view of the detail II according to FIG. 1, depicting a tool tip in different positions.
Figure 3:
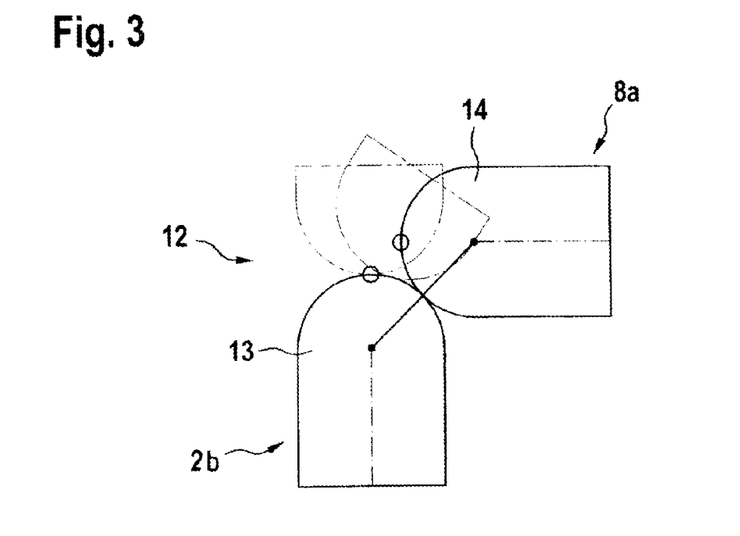
FIG. 3 shows a schematic view of a joint for the deflection of the tool tip.
Figure 4:
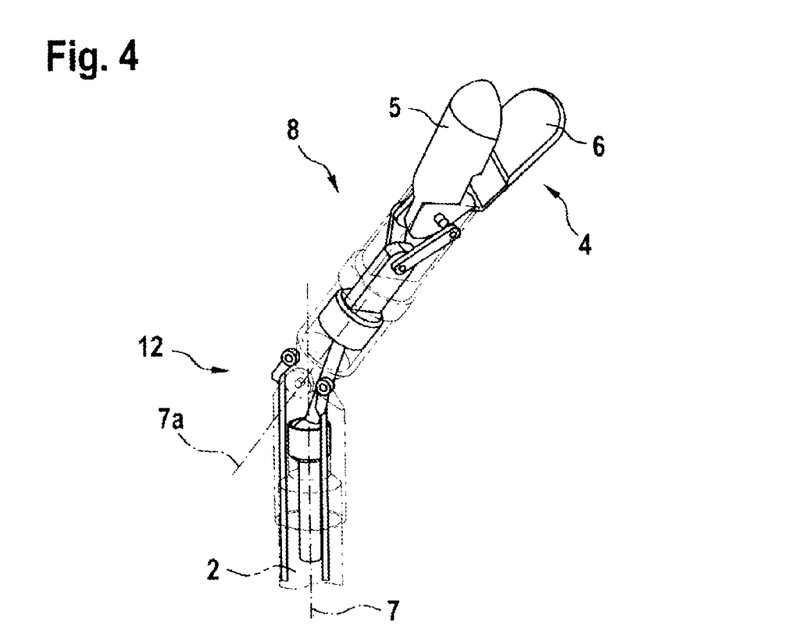
FIG. 4 shows a perspective and partially sectional view of the tool tip according to FIG. 2.

The joint 12 shown in FIGS. 2 to 5, serving for the deflection of the tool tip 8, is configured such that the distal end 2b of the shaft 2 and the proximal end 8a of the tool tip 8 are configured arc-shaped, i.e. in the shape of segments of a circle, and the two arcs (circle segments) 13 and 14 roll on each other in order to deflect the tool tip 8, as will be seen in particular from the schematic drawing in FIG. 3. During this rolling movement of the arcs 13 and 14 on each other, no lengthwise offset of the drivetrain 11 occurs. This means that, even during the deflection of the tool tip 8, the joint 12 of the drivetrain 11 remains in the same position relative to the shaft 2 and to the tool tip 8, and there is also no enforced actuation of the jaw parts 5 and 6 during the deflection of the tool tip 8.

During the deflection of the tool tip 8, the point where the tool tip 8 and the shaft 2 touch each other moves on an arc of a circle. In order to maintain the tool tip 8 in a defined position relative to the shaft 2, the friction between the tool tip 8 and the shaft 2 therefore has to be very high, or else a form-fit connection has to be produced.

Figure 5:
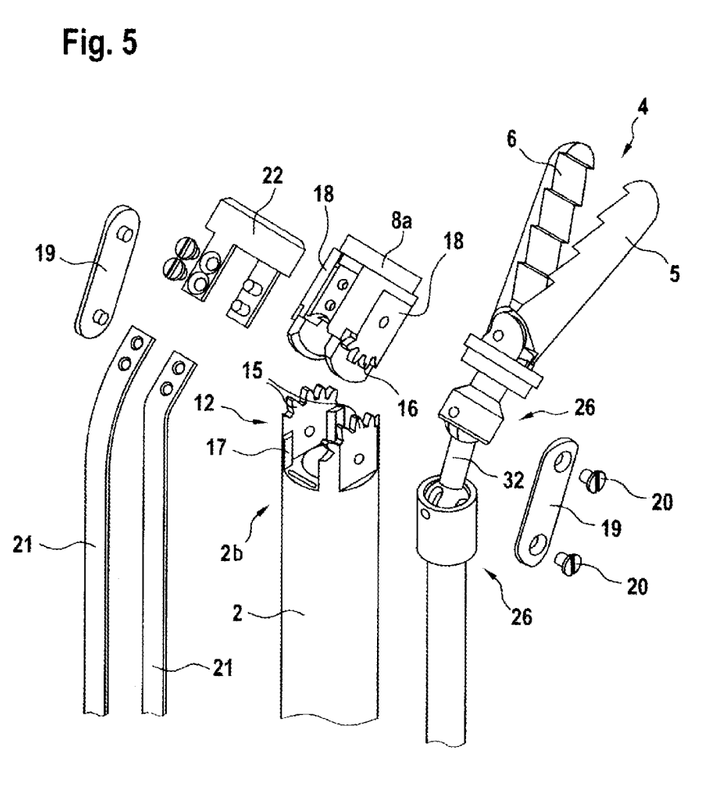
FIG. 5 shows a perspective and partially exploded view of the tool tip according to FIG. 4.

As will be seen from FIG. 5, in the illustrative embodiment for configuration of the joint 12 for the deflection of the tool tip 8, the two arcs 13 and 14 are configured as gearwheel profiles 15 and 16 that roll on each other. The form-fit and frictional engagement occurring between the teeth on both sides makes it possible to maintain the tool tip 8 in a wide variety of deflected positions.

While the proximal end 8a of the tool tip 8 in the embodiment shown in FIG. 5 is configured as a separate structural part, it is of course also possible for the proximal end 8a to be configured in one piece with the tool tip 8.

To configure the tooth profiles 15 and 16, the distal end 2b of the shaft 2 and the proximal end 8a of the tool tip 8 are each configured bifurcated, having two webs 17 and 18 arranged at a distance from and parallel to each other. The gearwheel profiles 15 and 16 are configured at the free ends of the webs 17 and 18 of the shaft 2 and of the tool tip 8.

By virtue of the fact that the gearwheel profiles 15 and 16 forming the joint 12 for deflection of the tool tip 8 are shifted to the lateral webs 17 and 18 of the bifurcated ends, sufficient space remains in the middle of the shaft 2 and of the tool tip 8 for passage of the drivetrain 11 for the tool tip 8.

As will also be seen from FIGS. 2 and 5, the distal end 2b of the shaft 2 and the proximal end 8a of the tool tip 8 are connected to each other by two brackets 19, which are fixed to the webs 17 and 18 at the midpoints of the gearwheel profiles 15 and 16 via screws 20. The brackets 19 hold the two sets of gearwheel profiles 15 and 16 at a constant spacing from each other and thereby ensure a uniform rolling of the gearwheel profiles 15 and 16 on each other, substantially free of play, during the deflection of the tool tip 8.

In the embodiment shown in FIG. 5, the deflection of the tool tip 8 with respect to the longitudinal axis 7 of the shaft 2 is activated via two pull/push elements 21 which are guided in the shaft 2 and are fixed at the distal end to the tool tip 8. In this embodiment, the fixing of the pull/push elements 21 to the tool tip 8 is effected via a securing ring 22 which can be fitted onto the tool tip 8 and which additionally serves to fix the drivetrain 11 relative to the shaft 2 in the axial direction.

At the proximal end, the pull/push elements 21 are operatively connected to the handle 3. Advantageously, the pull/push elements 21 are configured as rectangular nitinol bands. The smooth surfaces of the bands can be easily cleaned and, on account of their rectangular shape, utilize the available installation space in the shaft 2 better than, for example, circular control cables.

FIGS. 6 to 9 show two illustrative embodiments for the configuration of the drivetrain 11 via which the axial and rotational movements of the actuation elements 9 and 10 mounted in the shaft 2 are transmitted to the deflectable tool tip 8, so as to be able to adjust the jaw parts 5 and 6 of the tool 4 between an open and a closed position and in addition to permit a rotation of the tool tip 8 about the longitudinal axis 7 of the shaft 2 respectively the longitudinal axis 7a of the tool tip 8.

To be able to transmit the movements of the actuation elements 9 and 10 to the tool tip 8 deflected by an angle of up to 90°, the drivetrain 11 also has to be configured such that it can transmit the rotational and translatory movements when the drivetrain 11 is deflected likewise by up to 90°.

Figure 6:
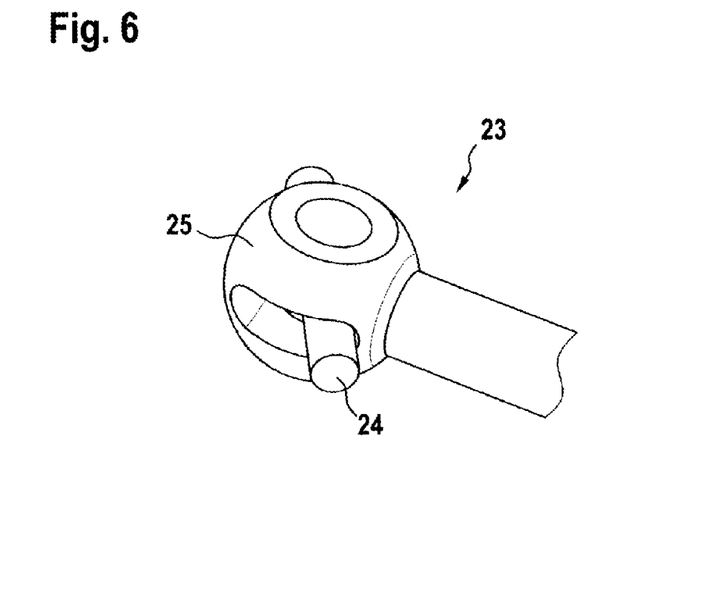
FIG. 6 shows a perspective view of a first embodiment for configuration of the joints of the drivetrain for actuation of the tool tip.
Figure 7:
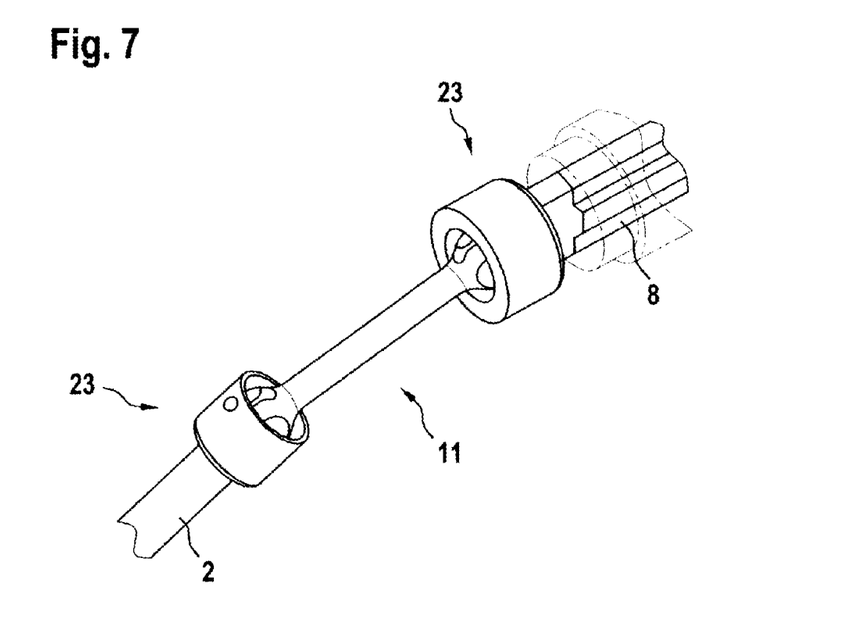
FIG. 7 shows a perspective view of two joints according to FIG. 6 connected in series.

In the first embodiment shown in FIGS. 6 and 7 for configuration of the drivetrain 11, the drivetrain 11 is composed of two identical joints which are connected in series one behind the other and are configured as CVD cardan joints 23.

Similarly to a known cardan joint, the constant velocity drive (CVD) joint 23 is based on a rotary cross 24 which however, in contrast to the known cardan joint, is not mounted in bifurcated recesses of the bearing axle but instead runs inside a holed ball 25. Since the CVD joint 23 is located inside the holed ball 25, the CVD joint 23 can withstand very high forces by virtue of the ball shape. The CVD joint 23 can transmit pushing and pulling forces while it is tilted about two axes.

Each CVD joint 23 in itself permits the transmission of pushing and pulling movements and rotation movements when the CVD joint 23 is deflected by an angle of up to 45°. Therefore, since at least two identical CVD joints 23 are connected in series, a deflection of at least 90° is attainable.

Figure 8:
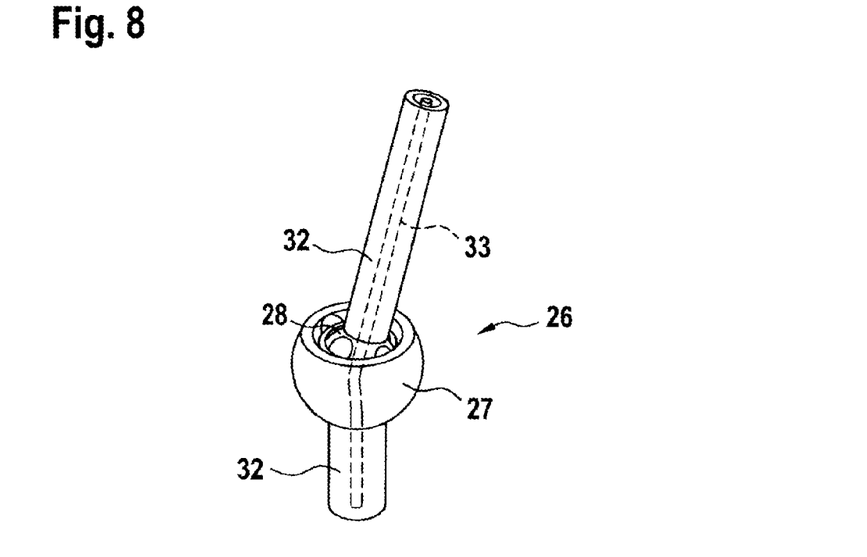
FIG. 8 shows a perspective view of a second embodiment for configuration of the joints of the drivetrain for actuation of the tool tip.
Figure 9:
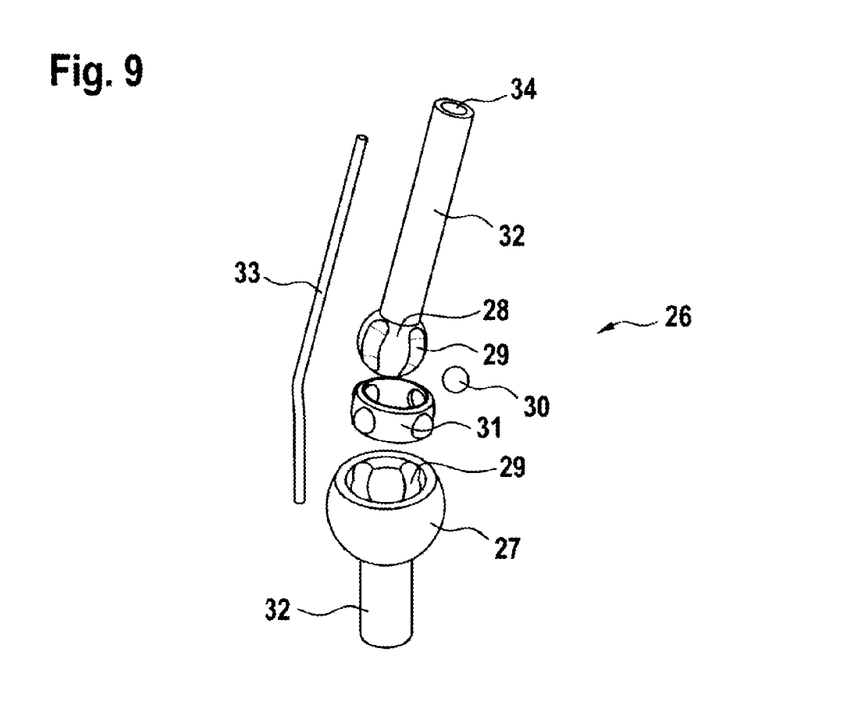
FIG. 9 shows a perspective exploded view according to FIG. 8.

According to the alternative second embodiment shown in FIGS. 8 and 9 for configuration of the drivetrain 11, the drivetrain 11 is composed of two identical joints which are connected in series one behind the other and are configured as homokinetic joints 26.

Homokinetic joints are characterized by the fact that they permit uniform transmission of angular velocity and torque from one shaft to a shaft arranged at an angle to the latter. The homokinetic joints 26 are composed of a ball socket 27 and a ball head 28, which seats in the ball socket 27. Both structural parts 27, 28 have up to six grooves 29 which are formed axially along the ball surfaces of ball socket 27 and ball head 28, wherein a groove 29 of the ball head 28 and a groove 29 of the ball socket 27 in each case form a groove pairing, in which a ball 30 is guided in a constrained manner. In addition, all balls 30 of each homokinetic joint 26 are guided in a common ball cage 31.

Each homokinetic joint 26 in itself permits the transmission of a torque in the event of a deflection between input and output shaft of up to 45°. Therefore, since at least two identical homokinetic joints 26 are connected in series, a deflection of at least 90° is attainable. With the customary homokinetic joints 26, axial forces are transmissible only to a slight extent on account of the grooves 29 of the ball tracks extending in the axial direction.

In order to markedly improve the transmission of axial forces by means of a homokinetic joint 26 in the embodiment shown, a ball head 28 and a ball socket 27 of each homokinetic joint 26 are connected to each other via a wire 33 which is arranged in the interior of the homokinetic joint 26 and is mounted in the cardan shafts 32. An axial bore 34 in the ball socket 27 and in the ball head 28 guides the wire 33, wherein the wire 33 is connected to both components, i.e. the ball socket 27 and the ball head 28.

By virtue of the wire 33 internally bridging the homokinetic joint 26, the ball socket 27 and the ball head 28 are fixed to each other in such a way that, without limiting the mobility of the homokinetic joint, high axial forces can now also be transmitted by means of a homokinetic joint 26 thus modified.

A medical instrument 1 configured as described above is characterized in that its joints 23, 26 ensure a high transmission force, along with the greatest possible number of degrees of freedom and a small installation space, and are also easy to clean.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE SIGNS 1 medical instrument
2 shaft
2a proximal end (of the shaft)
2b distal end (of the shaft)
3 handle
4 tool
5 jaw part
6 jaw part
7 longitudinal axis (of the shaft)
7a longitudinal axis (of the tool tip)
8 tool tip
8a proximal end (of the tool tip)
9 actuation element
10 actuation element
11 drivetrain
12 joint
13 arc (of the shaft)
14 arc (of the tool tip)
15 tooth profile (of the shaft)
16 tooth profile (of the tool tip)
17 web (of the shaft)
18 web (of the tool tip)
19 bracket
20 screw
21 pull/push element
22 securing ring
23 CVD joint
24 rotary cross
25 ball
26 homokinetic joint
27 ball socket
28 ball head
29 groove
30 ball
31 ball cage
32 cardan shaft
33 wire
34 bore

We claim:

1. A medical instrument with a hollow shaft, at the proximal end of which a handle is arranged, and at the distal end of which a tool with two jaw parts is arranged, of which at least one jaw part is pivotable relative to the other jaw part, wherein a distal end region of the shaft that carries the tool is configured as a tool tip that can be deflected with respect to the longitudinal axis of the shaft respectively with respect to a remaining rigid region of the shaft, and the tool tip is rotatable about the longitudinal axis of the shaft respectively about the longitudinal axis of the tool tip, and wherein the at least one pivotable jaw part of the tool is adjustable between a closed position and an open position, wherein the rotation of the tool tip and actuation of the jaw parts between the closed position and the open position takes place via two actuation elements which are mounted in the shaft and which are coupled at their proximal ends to the handle, characterized in that, in order to configure a joint for the deflection of the tool tip, the distal end of the rigid region of the shaft and the proximal end of the tool tip are configured arc-shaped in opposite directions, and the two arcs roll on each other in direct contact for the deflection of the tool tip, and in that the movements of the actuation elements, for rotating the tool tip and for actuating the jaw parts, are conveyed from the shaft into the deflectable tool tip via at least two identical joints, which are connected in series one behind the other and which can transmit rotation movements and also translatory movements, wherein the at least two joints connected in series one behind the other are configured as homokinetic joints and wherein in order to transmit axial forces, a ball head and a ball socket of each homokinetic joint are connected to each other via a wire which is arranged in the interior of each homokinetic joint and is mounted in cardan shafts.

2. The medical instrument according to claim 1, characterized in that the two arcs are configured as gearwheel profiles that roll on each other.

3. The medical instrument according to claim 2, characterized in that the distal end of the rigid region of the shaft and the proximal end of the tool tip are each configured bifurcated, having two webs arranged at a distance from and parallel to each other, wherein the gearwheel profiles are configured at free ends of the webs of the shaft and of the tool tip.

4. The medical instrument according to claim 3, characterized in that the distal end of the rigid region of the shaft and the proximal end of the tool tip are connected to each other by two brackets, which are fixed to the webs at the midpoints of the gearwheel profiles.

5. The medical instrument according to claim 1, characterized in that the deflection of the tool tip is actuated via two pull/push elements which are guided in the shaft and which are fixed via their distal ends to the tool tip.

6. The medical instrument according to claim 5, characterized in that the pull/push elements are configured as nitinol bands.

7. The medical instrument according to claim 1, characterized in that each homokinetic joint comprises an axial bore in the ball socket and in the ball head that guides the wire.

8. The medical instrument according to claim 1, characterized in that the wire of each homokinetic joint is configured as a nitinol wire.

* * * * *